United States Patent [19]

Moser

[11] Patent Number: 5,332,814

[45] Date of Patent: Jul. 26, 1994

[54] PROCESS FOR THE PREPARATION OF CARBACYCLIC NUCLEOSIDES, AND INTERMEDIATES

[75] Inventor: Heinz Moser, Möhlin, Switzerland

[73] Assignee: Ciba-Geigy Corporation, Ardsley, N.Y.

[21] Appl. No.: 969,631

[22] Filed: Oct. 30, 1992

[30] Foreign Application Priority Data

Nov. 12, 1991 [CH] Switzerland ............ 3292/91

[51] Int. Cl.[5] .............. C07D 473/18; C07D 473/02; C07D 239/47; C07D 239/553
[52] U.S. Cl. .................. 544/229; 544/254; 544/264; 544/265; 544/266; 544/271; 544/272; 544/276; 544/277; 544/280; 544/311; 544/312; 544/313; 544/314; 544/317; 546/14; 546/118; 549/15; 549/228; 549/363; 549/214; 568/838
[58] Field of Search ............... 544/254, 264, 266, 271, 544/272, 276, 277, 280, 311, 312, 313, 314, 317, 229, 265; 546/118, 14

[56] References Cited

FOREIGN PATENT DOCUMENTS 266099 5/1988 European Pat. Off. .
8707300 12/1987 PCT Int'l Appl. .
8908146 9/1989 PCT Int'l Appl. .
9106556 5/1991 PCT Int'l Appl. .

OTHER PUBLICATIONS

Hanessian, Tet. Let. 1971, p813.
Hanessian, Can J. Chem 50, 233(1972).
Palomino, Tet. Let 30, 6797 (1989).
King Tet. Let. 28, 3919 (1987).
Aldrich 1990 Catalog, p. 316.
Lowe et al Journal of the Chemical Society Chemical Communications No. 23, 1983 pp. 1392-1394.
Biggadike et al Journal of the Chemical Society. Chemical Communications No. 14, 1987, pp. 1083-1084.
Bodenteich et al Nucleosides & Nucleotides, 6 (1&2) pp. 233-237 (1990).
Szenzo, Tetrahedron Letter, vol. 31, No. 10 pp. 1463-1466 (1990).
Biggadike J. Chem. Soc. Chem. Commun pp. 1083-1084 (1987).
Balzarini et al J. Med. Chem. vol. 32, pp. 1861-1965 (1989).
Beres et al J. Med. Chem. vol. 33, pp. 1353-1360 (1990).
Marguez Med. Res. Rev. vol. 6(1) pp. 1-40 (1986).

Primary Examiner—Mark L. Berch
Attorney, Agent, or Firm—Kevin T. Mansfield; George R. Dohmann

[57] ABSTRACT

Process for the preparation of racemic compounds of the formula I

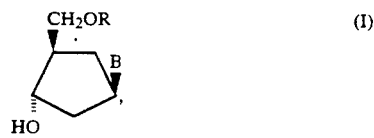

or enantiomers thereof, in which B is the radical of a nucleic base from the series comprising purine, a purine analogue or a pyridine analogue, and R is H or a protective group $R_1$, by reacting a) a compound of the formula II or enantiomer thereof

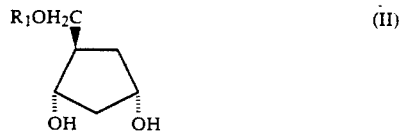

with a compound of the formulae X—CO—X, X—CS—X, X—SO—X, X—SO$_2$—X, $R_2$—NCO, $R_3R_4N$—C(O)—$R_5$, $X_2P$—$R_6$ or $X_2P(O)$—$R_6$, in which X is a leaving group, $R_2$ is, for example, $C_1$-$C_{18}$alkyl, $R_3$ and $R_4$ are, for example, H or $C_1$-$C_{18}$alkyl, $R_5$ is, for example, H or $C_1$-$C_{12}$alkyl, and $R_6$ is, for example, $C_1$-$C_{12}$alkyl or $C_1$-$C_{12}$alkoxy, to give a compound of the formula III or enantiomers thereof (Abstract continued on next page.)

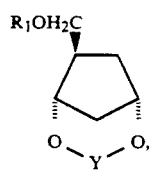 (III)

in which Y is the groups —C(O)—, —C(S)—, —SO—, —SO$_2$—, R$_2$NH—CH=, R$_3$R$_4$N—CR$_5$=, R$_6$P= and R$_6$(O)P=;

b) the further reaction of the compounds of the formulae III or enantiomers thereof with a nucleic base B on its own or together with a non-nucleophilic base, or with an alkali metal salt of the nucleic base B, to give compounds of the formula IV or enantiomers thereof

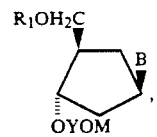 (IV)

in which M is H, an alkali metal or a non-nucleophilic base, and c) the conversion of the compounds of the formulae IV into the compounds of the formulae I by elimination of the protective group R$_1$ and of the group YOM. The reaction b) is regioselective and diastereoselective, and the compounds of the formula I are obtained in high yields and purities.

37 Claims, No Drawings

PROCESS FOR THE PREPARATION OF CARBACYCLIC NUCLEOSIDES, AND INTERMEDIATES

The invention relates to a process for the preparation of carbacyclic nucleosides by reacting protected and bridged transhydroxymethyl-cis-1,3-pentanediols with a nucleic base from the series comprising purine, purine analogues and pyrimidine analogues, followed by elimination of the bridging and protective group.

Carbacyclic nucleoside analogues have become interesting because of their antiviral properties and as units for oligonucleotides having antisense properties, see, for example, M. Bodenteich et al., *Nucleosides & Nucleotides*, 6(182), pages 233-237 1987, A. Szemzo et al., *Tetrahedron Letters*, Vol. 31, No. 10, pages 1463-1466 (1990), K. Biggadike et al., *J. Chem. Soc., Chem. Commun.*, pages 1083-1084 (1987), J. Balzarini et al., *J. Med. Chem.*, Vol. 32, pages 1861-1865 (1989), J. Beres et al., *J. Med. Chem.*, Vol. 33, pages 1353-1360 (1990) and V. E. Marquez et al., *Med. Res. Rev.*, Vol. 6, pages 1-40 (1986). The known methods for synthesis are very complicated multi-step processes by means of which the desired nucleoside analogues are obtained in low total yields only. No satisfactory process has been found so far for the synthesis of the carbacyclic nucleoside analogues in high yields, both racemic and enantiomerically pure. A process for the simultaneous preparation of such nucleoside analogues of the natural and unnatural series using one starting material is not known either.

It has now been found that such nucleoside analogues can be prepared in high yields and purities, both in racemic and enantioselective form, when the starting material used are the protected trans-4-hydroxymethyl-cis-1,3-pentanediols, which are readily accessible from cis-1,3-pentenediol by a novel process, in the form of the racemates or the enantiomers thereof, the 1,3-hydroxyl groups are bridged with, for example, $SO_2$ groups, these compounds are reacted with a nucleic base such as, for example, adenine, and the bridging and protective groups are then eliminated in a manner known per se. This multi-step process allows the simultaneous synthesis of nucleoside analogues of the natural and unnatural series and the racemates, the total yields being high despite the fact that a plurality of steps are involved in the synthesis. The process is therefore also suitable for industrial production.

The invention relates to a process for the preparation of racemic compounds of the formula I

or of the enantiomers of the formulae (Ia) and (Ib)

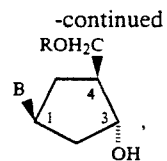

in which B is the radical of a nucleic base from the series comprising purine or a purine analogue or pyrimidine analogue and R is H or a protective group $R_1$, which comprises a) reacting a compound of the formula II in the form of the racemate or of the enantiomers thereof, of the formulae IIa or IIb

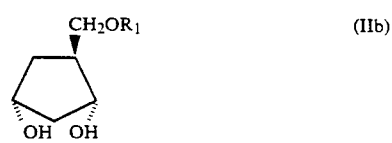

in which $R_1$ is a protective group, with a compound of the formulae X—CO—X, X—CS—X, X—SO—X, X—$SO_2$—X, $R_2$—NCO, $R_3R_4N$—C(O)—$R_5$, $X_2P$—$R_6$ or $X_2P(O)$—$R_6$, in which X is a leaving group, $R_2$ is linear or branched $C_1$-$C_{18}$alkyl, $C_5$-$C_8$cycloalkyl, phenyl, benzyl, or phenyl or benzyl which are substituted by $C_1$-$C_6$alkyl or $C_1$-$C_6$alkoxy, $R_3$ and $R_4$ independently of one another are H, linear or branched $C_1$-$C_{18}$alkyl, $C_5$-$C_8$cycloalkyl, phenyl, benzyl, or phenyl or benzyl which are substituted by $C_1$-$C_6$alkyl or $C_1$-$C_6$alkoxy, or $R_3$ and $R_4$ together are tetramethylene, pentamethylene or 3-oxa-1,5-pentylene, $R_5$ is H, linear or branched $C_1$-$C_{12}$alkyl, $C_5$-$C_8$cycloalkyl, phenyl, benzyl, or phenyl or benzyl which are substituted by $C_1$-$C_6$alkyl or $C_1$-$C_6$alkoxy, and $R_6$ is linear or branched $C_1$-$C_{12}$alkyl or $C_1$-$C_{12}$alkoxy, $C_5$-$C_8$cycloalkyl or $C_5$-$C_8$cycloalkoxy, phenyl or phenyloxy, benzyl or benzyloxy, or $R_6$ is phenyl or phenyloxy or benzyl or benzyloxy which are substituted by $C_1$-$C_6$alkyl or $C_1$-$C_6$alkoxy, to give racemates of the formula III or enantiomers of the formula IIIa or IIIb,

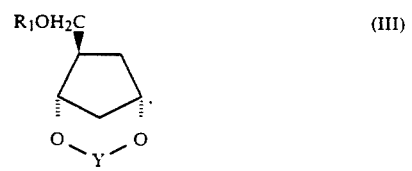

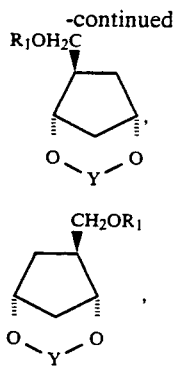

in which Y is the groups —C(O)—, —C(S)—, —SO—, —SO$_2$, R$_2$NH—CH=, R$_3$R$_4$N—CR$_5$=, R$_6$P= and R$_6$(O)P= in which R$_1$ and R$_2$ to R$_6$ are as defined above, b) reacting the compounds of the formulae III, IIIa or IIIb with a nucleic base B, without or together with a non-nucleophilic base, or alkali metal salts of a nucleic acid B, to give racemates of the formula IV or enantiomers of the formula IVa or IVb

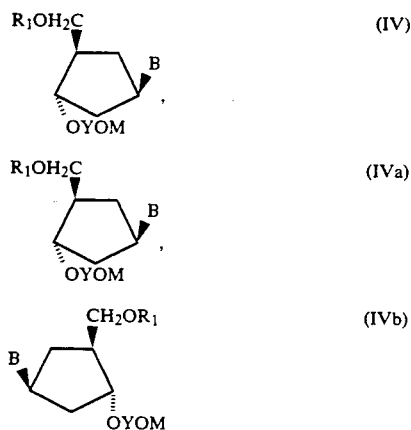

in which M is H, an alkali metal or a non-nucleophilic base and Y is as defined above, and c) converting the compounds of the formulae IV, IVa and IVb into the compounds of the formulae I, Ia and Ib by eliminating the protective group R$_1$ and the group YOM.

Protective groups and processes for the derivatisation of the hydroxyl groups with such protective groups are generally known in sugar chemistry. Examples of such protective groups are: linear or branched C$_1$-C$_8$alkyl, in particular C$_1$-C$_4$alkyl, for example methyl, ethyl, n- and i-propyl, n-, i- and t-butyl; C$_7$-C$_{12}$aralkyl, for example benzyl, methylbenzyl, dimethylbenzyl, methoxybenzyl, dimethoxybenzyl, bromobenzyl; diphenylmethyl, di(methylphenyl)methyl, di(dimethylphenyl)methyl, di(methoxyphenyl)methyl, di(dimethoxyphenyl)methyl, trityl, tri(methylphenyl)methyl, tri(dimethylphenyl)methyl, tri(methoxyphenyl)methyl, tri(dimethoxyphenyl)methyl, monomethoxytrityl, dimethoxytrityl; pixyl; triphenylsilyl, alkyldiphenylsilyl, dialkylphenylsilyl and trialkylsilyl having 1 to 20, preferably 1 to 12, particularly preferably 1 to 8 C atoms in the alkyl groups, for example trimethylsilyl, triethylsilyl, tri-n-propylsilyl, i-propyl-dimethylsilyl, t-butyldimethylsilyl, t-butyldiphenylsilyl, n-octyldimethylsilyl, (1,1,2,2-tetramethylethyl)dimethylsilyl; C$_2$-C$_{12}$acyl, in particular C$_2$-C$_8$acyl, for example acetyl, propanoyl, butanoyl, pentanoyl, hexanoyl, benzoyl, methylbenzoyl, methoxybenzoyl, chlorobenzoyl and bromobenzoyl; R$_{17}$—SO$_2$—, in which R$_{17}$ is C$_1$-C$_{12}$alkyl, in particular C$_1$-C$_6$alkyl, C$_5$- or C$_6$cycloalkyl, phenyl, benzyl, C$_1$-C$_{12}$alkylphenyl and in particular C$_1$-C$_4$alkylphenyl, or C$_1$-C$_{12}$alkylbenzyl and in particular C$_1$-C$_4$alkylbenzyl, or halophenyl or halobenzyl, for example methyl-, ethyl-, propyl-, butyl-, phenyl-, benzyl-, p-bromo-, p-methoxy- and p-methylphenylsulfonyl; C$_1$-C$_{12}$alkoxycarbonyl, preferably C$_1$-C$_8$alkoxycarbonyl, for example methoxy-, ethoxy-, n- or i-propoxy- or n-, i- or t-butoxycarbonyl, or phenyloxycarbonyl, benzyloxycarbonyl, methyl- or methoxy- or chlorophenyloxycarbonyl or -benzyloxycarbonyl.

In a preferred embodiment, the compounds of the formula I are those in which R$_1$ radicals independently of one another are linear or branched C$_1$-C$_4$alkyl, C$_7$-C$_{12}$aralkyl, trialkylsilyl having 1 to 12 C atoms in the alkyl groups, C$_2$-C$_8$acyl, R$_{17}$—SO$_2$—, in which R$_{17}$ is C$_1$-C$_6$alkyl, phenyl, benzyl, C$_1$-C$_4$alkylphenyl, C$_1$-C$_4$alkylbenzyl or halophenyl or halobenzyl, or they are C$_1$-C$_8$alkoxycarbonyl, phenoxycarbonyl or benzyloxycarbonyl.

In a particularly preferred embodiment, R$_1$ is methyl, ethyl, n- and i-propyl, n-, i- and t-butyl; benzyl, methylbenzyl, dimethylbenzyl, methoxybenzyl, dimethoxybenzyl, bromobenzyl; diphenylmethyl, di(methylphenyl)methyl, di(dimethylphenyl)methyl, di(methoxyphenyl)methyl, di(dimethoxyphenyl)methyl, trityl, tri(methylphenyl)methyl, tri(dimethylphenyl)methyl, tri(methoxyphenyl)methyl, tri(dimethoxyphenyl)methyl, monomethoxytrityl, dimethoxytrityl, pixyl; trimethylsilyl, triethylsilyl, tri-n-propylsilyl, i-propyl-dimethylsilyl, t-butyl-dimethylsilyl, t-butyl-diphenylsilyl, n-octyldimethylsilyl, (1,1,2,2-tetramethylethyl)-dimethylsilyl; acetyl, propanoyl, butanoyl, pentanoyl, hexanoyl, benzoyl, methylbenzoyl, methoxybenzoyl, chlorobenzoyl and bromobenzoyl; methyl-, ethyl-, propyl-, butyl-, phenyl-, benzyl-, p-bromo-, p-methoxy- and p-methylphenylsulfonyl; methoxy-, ethoxy-, n- or i-propoxy- or n-, i- or t-butoxycarbonyl, or phenyloxycarbonyl, benzyloxycarbonyl, methyl- or methoxy- or chlorophenyloxycarbonyl or-benzyloxycarbonyl.

If B is a purine radical or an analogue thereof, it can be a radical of the formula V, Va, Vb, Vc, Vd or Ve,

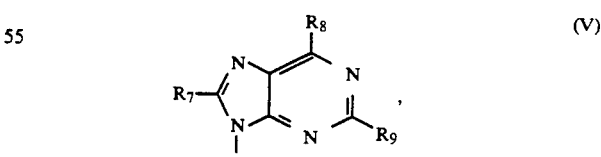

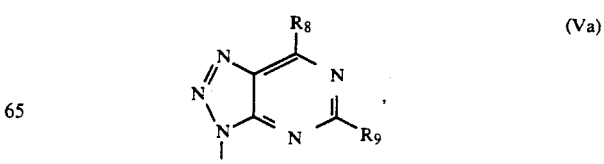

-continued

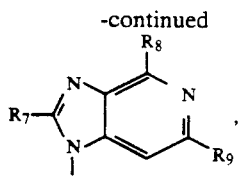 (Vb)

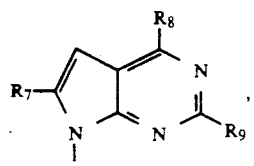 (Vc)

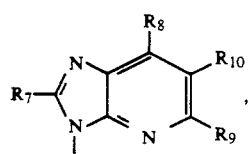 (Vd)

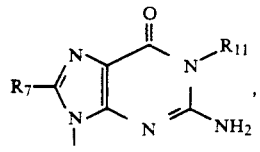 (Ve)

in which $R_7$ is H, Cl, Br, $NH_2$ or OH, and $R_8$, $R_9$ and $R_{10}$ independently of one another are H, OH, SH, $NH_2$, $NHNH_2$, NHOH, NHOalkyl having 1 to 12 C atoms, F, Cl, Br, alkyl or hydroxyalkyl or aminoalkyl or alkoxy or alkylthio having 1 to 12 C atoms, the hydroxyl and amino groups being unsubstituted or substituted by a protective group, phenyl, benzyl, primary amino having 1 to 20 C atoms or secondary amino having 2 to 30 C atoms, and $R_{11}$ is H or $C_1$-$C_4$alkyl.

Suitable protective groups have been mentioned above. Preferred protective groups are $C_1$-$C_8$acyl groups such as acetyl, propionyl, butyroyl and benzoyl. $R_{11}$ is preferably H or methyl.

The primary amino has preferably 1 to 12, particularly preferably 1 to 6, C atoms, and the secondary amino has preferably 2 to 12, particularly preferably 2 to 6, C atoms.

Some examples of alkyl, alkoxy, alkylthio, hydroxyalkyl and aminoalkyl, all of which preferably contain 1 to 6 C atoms, are methyl, ethyl and the isomers of propyl, butyl, pentyl, hexyl, heptyl, octyl, nonyl, decyl, undecyl and dodecyl, and corresponding alkoxy, alkylthio, hydroxyalkyl and aminoalkyl radicals. Alkyl, alkoxy, alkylthio, hydroxyalkyl and aminoalkyl particularly preferably contains 1 to 4 C atoms. Preferred alkyl, alkoxy, alkylthio, hydroxyalkyl and aminoalkyl radicals are methyl, ethyl, n- and i-propyl, n-, i- and t-butyl, methoxy, ethoxy, methylthio and ethylthio, aminomethyl, aminoethyl, hydroxymethyl and hydroxyethyl.

Primary amino and secondary amino can be, for example, a radical of the formula $R_{14}R_{15}N$ in which $R_{14}$ is H or independently has the meaning of $R_{15}$, and $R_{15}$ is $C_1$-$C_{20}$-, preferably $C_1$-$C_{12}$- and particularly preferably $C_1$-$C_6$alkyl, -aminoalkyl, -hydroxyalkyl; carboxyalkyl or carbalkoxyalkyl, the carbalkoxy group having 2 to 8 C atoms and the alkyl group having 1 to 6, preferably 1 to 4, C atoms; $C_2$-$C_{20}$-, preferably $C_2$-$C_{12}$-, and particularly preferably $C_2$-$C_6$alkenyl; phenyl, mono- or di(C$_1$-$C_4$alkyl- or -alkoxy)phenyl, benzyl, mono- or di(C$_1$-$C_4$alkyl- or -alkoxy)benzyl; or 1,2-, 1,3- or 1,4-imidazolyl-$C_1$-$C_6$alkyl, or $R_{14}$ and $R_{15}$ together are tetra- or pentamethylene, 3-oxa-1,5-pentylene, —CH$_2$—NR$_{16}$—CH$_2$CH$_2$— or —CH$_2$CH$_2$—NR$_{16}$—CH$_2$CH$_2$—, in which $R_{16}$ is H or $C_-$$_{C4}$alkyl. The amino group in aminoalkyl can be substituted by one or two $C_-$$_{C4}$alkyl or -hydroxyalkyl groups. The hydroxyl group in hydroxyalkyl can be etherified with $C_-$$_{C4}$alkyl.

Examples of alkyl have been given above. Examples of aminoalkyl are aminomethyl, aminoethyl, 1-aminoprop-2-yl or -3-yl, 1-amino-but-2-yl or -3-yl or -4-yl, N-methyl- or N,N-dimethyl- or N-ethyl- or N,N-diethyl- or N-2-hydroxyethyl- or N,N-di-2-hydroxyethylaminomethyl or -aminoethyl or -aminopropyl or -aminobutyl. Examples of hydroxyalkyl are hydroxymethyl, 1-hydroxy-eth-2-yl, 1-hydroxy-prop-2- or -3-yl, 1-Hydroxy-but-2-yl, -3-yl or -4-yl. Examples of carboxyalkyl are carboxymethyl, carboxyethyl, carboxypropyl and carboxybutyl, and examples of carbalkoxyalkyl are these carboxyalkyl groups which are esterified with methyl or ethyl. Examples of alkenyl are allyl, but-1-en-3-yl or -4-yl, pent-3- or 4-en-1-yl or -2-yl, hex-3- or -4- or -5-en-1-yl or -2-yl. Examples of alkyl- and alkoxyphenyl, and -benzyl, respectively, are methylphenyl, dimethylphenyl, ethylphenyl, diethylphenyl, methylbenzyl, dimethylbenzyl, ethylbenzyl, diethylbenzyl, methoxyphenyl, dimethoxyphenyl, ethoxyphenyl, diethoxyphenyl, methoxybenzyl, dimethoxybenzyl, ethoxybenzyl, diethoxybenzyl. Examples of imidazolylalkyl in which the alkyl group preferably contains 1 to 4 C atoms are 1,2-, 1,3- or 1,4-imidazolylethyl or -n-propyl or -n-butyl. $R_{16}$ is preferably H, methyl or ethyl.

Preferred examples of primary amino and secondary amino are methyl-, ethyl-, dimethyl-, diethyl-, allyl-, mono- or di-(1-hydroxy-eth-2-yl)-, phenyl- and benzylamino, acetylamino and benzoylamino.

In a preferred embodiment, $R_7$ is hydrogen. In another preferred embodiment, $R_{10}$ is hydrogen. In a further preferred embodiment, $R_8$ and $R_9$ independently of one another are H, F, Cl, Br, OH, SH, $NH_2$, NHOH, $NHNH_2$, methylamino, dimethylamino, benzoylamino, methoxy, ethoxy and methylthio.

Some examples of analogues of the purine series are, besides purine, adenine, N-methyladenine, N-benzoyladenine, 2-methylthioadenine, 2-aminoadenine, 6-hydroxypurine, 2-amino-6-chloropurine, 2-amino-6-methylthiopurine, guanine, N-isobutyrylguanine. Particularly preferred are adenine, 2-aminoadenine and guanine.

If B in formula I is an analogue pyrimidine radical, then it is preferably a uracil, thymine and cytosine radical of the formulae VI, VIa and VIb

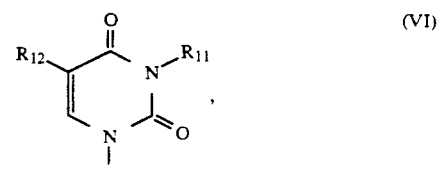 (VI)

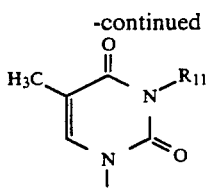

(VIa)

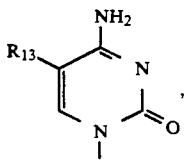

(VIb)

in which R$_{11}$ is H or C$_1$-C$_4$alkyl and R$_{12}$ and R$_{13}$ independently of one another are as defined above under R$_8$, including the preferred meaning, and the hydrogen atoms of the NH$_2$ group in formula VIb can be substituted by C$_1$-C$_6$alkyl or benzoyl, as well as the dihydro derivatives of the radicals of the formulae VI, VIa and VIb. R$_{12}$ is preferably H, C$_1$-C$_6$alkyl or hydroxyalkyl, F, Cl, Br, NH$_2$, benzoylamino, mono- or di-C$_1$-C$_6$alkylamino, and R$_{13}$ is preferably H, C$_1$-C$_6$alkyl or -alkoxy or -hydroxyalkyl, F, Cl, Br, NH$_2$, benzoylamino, mono- or di-C$_1$-C$_6$alkylamino.

R$_{11}$ is preferably H or methyl. R$_{12}$ is preferably H, F, Cl, Br, NH$_2$, NHCH$_3$, N(CH$_3$)$_2$ or C$_1$-C$_4$alkyl. R$_{13}$ is preferably H, C$_1$-C$_4$alkyl, in particular methyl, or NH$_2$, NHCH$_3$ or (CH$_3$)$_2$N.

Some examples of pyrimidine analogues are uracil, thymine, cytosine, 5-fluorouracil, 5-chlorouracil, 5-bromouracil, dihydrouracil and 5-methylcytosin.

R$_2$ is preferably C$_1$-C$_{12}$alkyl, particularly preferably C$_1$-C$_6$alkyl, C$_5$- or C$_6$cycloalkyl, phenyl, benzyl, or phenyl or benzyl which are substituted by C$_1$-C$_4$alkyl or C$_1$-C$_4$alkoxy. Some examples of R$_2$ are methyl, ethyl, n- or i-propyl, n- or i-butyl, cyclopentyl, cyclohexyl, phenyl, methylphenyl, ethylphenyl, i-propylphenyl, n- or t-butylphenyl, dimethylphenyl, methoxyphenyl and dimethoxyphenyl.

R$_3$ and R$_4$ are preferably H, C$_1$-C$_{12}$alkyl, particularly preferably C$_1$-C$_6$alkyl, C$_5$- or C$_6$cycloalkyl, phenyl, benzyl, or phenyl or benzyl which are substituted by C$_1$-C$_4$alkyl or C$_1$-C$_4$alkoxy. Some examples of R$_2$ are methyl, ethyl, n- or i-propyl, n- or i-butyl, cyclopentyl, cyclohexyl, phenyl, methylphenyl, ethylphenyl, i-propylphenyl, n- or t-butylphenyl, dimethylphenyl, methoxyphenyl and dimethoxyphenyl.

R$_5$ is preferably C$_1$-C$_6$alkyl, C$_5$- or C$_6$cycloalkyl, phenyl, benzyl, or phenyl or benzyl which are substituted by C$_1$-C$_4$alkyl or C$_1$-C$_4$alkoxy. Some examples of R$_2$ are methyl, ethyl, n- or i-propyl, n- or i-butyl, cyclopentyl, cyclohexyl, phenyl, methylphenyl, ethylphenyl, i-propylphenyl, n- or t-butylphenyl, dimethylphenyl, methoxyphenyl and dimethoxyphenyl.

R$_6$ is preferably C$_1$-C$_6$alkyl or -alkoxy, C$_5$- or C$_6$cycloalkyl or -cycloalkoxy, phenyl or phenyloxy, benzyl or benzyloxy, or is phenyl, phenyloxy, benzyl or benzyloxy which are substituted by C$_1$-C$_4$alkyl or C$_1$-C$_4$alkoxy. Some examples of R$_6$ are methyl, ethyl, n- or i-propyl, n- or iobutyl, methoxy, ethoxy, propyloxy, butyloxy, cyclopentyl, cyclohexyl, phenyl, phenoxy, methylphenyl, ethylphenyl, i-propylphenyl, n- or t-butylphenyl, dimethylphenyl, methoxyphenyl and dimethoxyphenyl. methylphenyloxy, ethylphenyloxy, i-propylphenyloxy, n- or t-butylphenyloxy, dimethyl-phenyloxy, methoxyphenyloxy and dimethoxyphenyloxy, benzyl, benzyloxy, methylbenzyl, methoxybenzyl, dimethylbenzyl and dimethoxybenzyl.

The leaving group X can be a halide, preferably chloride or bromide, C$_1$-C$_6$alkoxy, preferably C$_1$-C$_4$alkoxy, phenoxy, benzyloxy, or open-chain or cyclic secondary amino having 2 to 12 C atoms. Examples of secondary amino are dimethylamino, diethylamino, di-n-butylamino, diphenylamino, dibenzylamino, piperazinyl, morpholinyl or imidazolyl. Preferred leaving groups are chloride, bromide, methoxy, ethoxy and imidazolyl. The reaction of process step a) is preferably carried out using compounds of the formula X—CO—X in which X is imidazolyl, or with a compound of the formula X—SO—X in which X is Cl or Br, it being possible for the resulting cyclic sulfoxide compounds to be subsequently oxidised in a known manner to give the corresponding cyclic sulfodioxide compounds.

The invention furthermore relates to the compounds of the formulae II, IIa and IIb

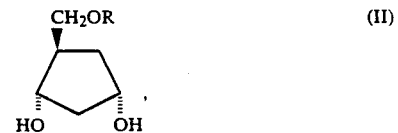

(II)

or the enantiomers of the formulae (Ia) and (Ib)

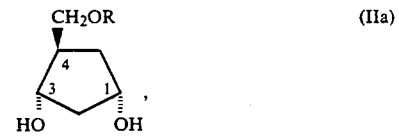

(IIa)

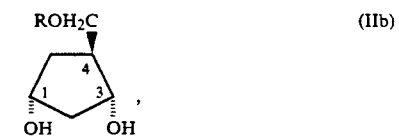

(IIb)

in which R is H or a protective group R$_1$. They can be prepared for example in the following manner:

In a first step, 1 equivalent of cis-1,3-pent-4-enediol of the formula A

(A)

is reacted with an equivalent of di-t-butylsilyl ditriflate [(t-butyl)$_2$Si(CF$_3$SO$_3$)$_2$] to give a compound of the formula B

(B)

which, in a second step, is hydroformylated with a mixture of H$_2$ and CO in the presence of a catalyst, for example RhCl[P(C$_6$H$_5$)$_3$]$_3$, at increased temperature, for example 60 to 150° C., and under pressure, to give a compound of the formula C

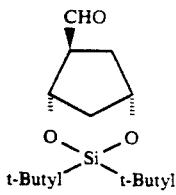

The compound of the formula C is hydrogenated, for example using $NaBHC_4$ or $LiAl318 H_4$, in the presence of an ether as the solvent, to give a compound of the formula D

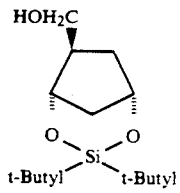

and the hydroxyl group of the compound of the formula D is then protected, for example by reaction with trityl chloride. The bridging group $(t\text{-butyl})_2Si=$ is eliminated from the protected compound of the formula D by treatment with tetra-n-butylammonium fluoride trihydrate, and the compounds of the formula E

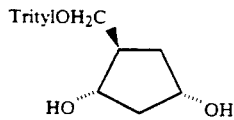

are obtained as a racemate. The trityl protective group can be eliminated in a known manner and replaced by other protective groups.

The racemate can be used directly or can be converted into an isomer mixture of the regio isomers of the formulae F and G by means of an enzymatically catalysed monoacylation reaction with vinyl acetate in the presence of Pseudomonas fluorescens lipase or Chromobacterium viscosum lipase:

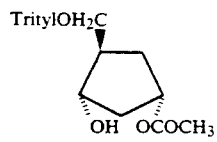

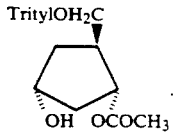

In this enzymatic reaction, sterically demanding protective groups are preferably used, for example unsubstituted or $C_1$-$C_4$alkyl- or $C_1$-$C_4$alkoxy-substituted diphenylmethyl, and, in particular, triphenylmethyl (trityl).

The isomer mixture obtained can be separated completely in a simple manner by silica gel chromatography. The reaction of the compounds of the formulae F and G with bases, for example ammonia, amines or alkali metal bases in alcoholic solution results to virtually quantitative optical yields of the enantiomeric diols of the formulae H and J,

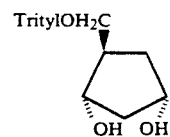

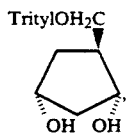

the compounds of the formula H being the (+) enantiomers of the natural series and, correspondingly, the compounds of the formula J the (−) enantiomers of the unnatural series. To prepare compounds of the formulae II, IIa and IIb in which R is H, the protective group is eliminated in a manner known per se.

The reaction of process steps a) can be carried out expediently in the presence of an inert solvent.

Examples of suitable inert solvents are polar or unpolar, preferably aprotic, solvents which can be used on their own or as mixtures of at least two solvents. Examples are: ethers (dibutyl ether, tetrahydrofuran, dioxane, ethylene glycol diethyl ether or ethylene glycol dimethyl ether, diethylene glycol dimethyl ether, diethylene glycol diethyl ether, triethylene glycol dimethyl ether), halogenated hydrocarbons (methylene chloride, chloroform, 1,2-dichloroethane, 1,1,1-trichloroethane, 1,1,2,2-tetrachloroethane), carboxylates and lactones (ethyl acetate, methyl propionate, ethyl benzoate, 2-methoxyethyl acetate, γ-butyrolactone, δ-valerolactone, pivalolactone), carboxamides and lactams (N,N-dimethylformamide, N,N-diethylformamide, N,N-dimethylacetamide, tetramethylurea, hexamethylphosphoric triamide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylene sulfone, tetramethylene sulfone), tertiary amines (triethylamine, N-methylpiperidine, N-methylmorpholine), aromatic hydrocarbons, for example benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile), as well as aliphatic or cycloaliphatic hydrocarbons (pentane, petroleum ether, hexane, cyclohexane and methylcyclohexane).

Preferred solvents are halogenated aliphatic hydrocarbons, aromatic hydrocarbons, ethers and nitriles, for example methylene chloride, chloroform, benzene, toluene, acetonitrile, diethyl ether, dibutyl ether, tetrahydrofuran and dioxane.

The reaction temperature in process step a) is preferably −20° C. to 200° C., particularly preferably 0° C. to 120° C.

The concomitant use of acid-binding agents, for example tertiary amines, has proved expedient if acids, for example HX, are formed in the reaction. Examples of suitable tertiary amines are trimethyl-, triethyl-, tripropyl- or tributylamine, di-i-propylethylamine, N-methylmorpholine, pyridine, collidine and lutidine. The acid-binding agents are preferably employed in excess, for example up to 10 mol equivalents, preferably up to 5 mol equivalents. When X—SO—X is used as reactant, the sulfoxide compound formed can be reacted without isolation with or without catalytic amounts of a noble metal salt, for example RuCl$_3$.H$_2$O, to give the corresponding sulfodioxide compounds by oxidation with, for example, alkali metal perchlorates, alkali metal perbromates or alkali metal periodates.

If desired, the compounds of the formulae II, IIa and IIb can be isolated by customary methods, for example distillation, crystallisation and/or chromatography.

The reactants used in process step a) are generally employed in equimolar amounts. The use of an excess of the reactant used for introducing group Y, for example up to 4, preferably up to 2.5, equivalents per equivalent of the compound of the formulae II, IIa and IIb, has proved advantageous.

The invention furthermore relates to the racemates of the formula III and to the enantiomers of the formula IIIa or IIIb,

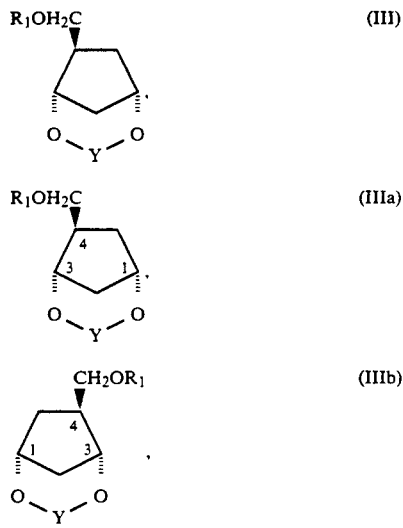

in which Y is the groups —C(O)—, —C(S)—, —SO—, —SO$_2$—, R$_2$NH—CH=, R$_3$R$_4$N—CR$_5$=, R$_6$P= and R$_6$(O)P= and R$_1$ to R$_6$ are as defined above, including the preferred meanings. Y is particularly preferably the group —C(O)—, —SO— or —SO$_2$—.

The reaction in process step b) is expediently carried out in the presence of an inert solvent. Suitable solvents have been mentioned above. Preferred solvents are polar and aprotic solvents, for example nitriles, in particular acetonitrile, propionitrile, butyronitrile, benzonitrile and phenylacetonitrile, N,N-dimethylated or -diethylated carboxamides or N-methylated or -ethylated lactams, for example dimethylacetamide and N-methylpyrrolidone, sulfoxides, for example dimethyl sulfoxide, or sulfones, for example tetramethylene sulfone.

The reaction is preferably carried out in the presence of agents which activate the reactive NH group of the nucleic base and/or form salts with acid groups —OYOH which have formed. Examples of such agents are non-nucleophilic, preferably lipophilic, bases which are soluble in the reaction medium, for example tertiary amines having preferably 3 to 18 C atoms (trimethylamine, triethylamine, tri-n-propylamine, tri-n-butylamine, N-methylpiperazine, azabicycloheptane, azabicycloheptene, azabicyclooctane, azabicyclooctene, 1,8diaza-bicyclo-[5,4,0]-undec-7-ene) or disilazanes having preferably C$_1$–C$_4$alkyl in the silyl groups (hexamethyldisilazane), all of which can be employed on their own or as a mixture. It is furthermore possible to metalate the reactive NH group with the aid of, for example, alkali metal hydrides, alkali metal alkoxides or lithium alkyl compounds (for example LiH, NaI, KH, LiCH$_3$ or LiC$_4$H$_9$). In a preferred embodiment, the reaction of process step b) is carried out in the presence of equimolar amounts, or a slight excess, of 1,8-diazabicyclo-[5,4,0]-undec-7-ene.

The reaction temperature in process step b) is, for example, from −20° to 200° C., preferably 0° to 150° C., particularly preferably 10° to 100° C.

The reaction in process step b) can be carried out, for example, in such a way that the nucleic base is suspended or dissolved in a solvent, a non-nucleophilic base is added, and the suspension is stirred until a clear solution forms. A compound of the formula III, IIIa or IIIb is then added to this solution, and the mixture is allowed to react until the reaction has ended. To isolate the compounds, the solvent is evaporated and the residue is purified by customary methods, for example chromatography and crystallisation. To carry out the reaction according to process step c), it is also possible to use the crude products. The reaction is surprisingly regiospecific and diastereospecific, which is why the desired compounds are obtained in high yields and purities.

The elimination of the protective group R$_1$ and the group YOM in the compounds of the formulae IV, IVa and IVb can take place simultaneously or in succession, depending on the protective group R$_1$ used. The group YOM can be eliminated hydrolytically, for example in a manner known per se by reaction with dilute aqueous mineral acids in alcoholic solution, it being possible for the reaction temperature to be, for example, 20° to 120° C. This results in nucleosides which are protected by the group R$_1$ and which can be in the form of salts of the mineral acids used, depending on the nucleoside base, and which can be used directly for eliminating the protective group or which can be isolated beforehand by customary methods. The free nucleosides can be obtained from the salts by treatment with alkali metal bases or with basic ion exchangers. Protective groups R$_1$ which can be detached hydrolytically can be eliminated simultaneously, and it may be expedient to use concentrated mineral acids for this purpose. Examples of suitable mineral acids are aqueous HCl, HBr or H$_2$SO$_4$. Other protective groups can be removed by methods generally known in sugar chemistry.

The compounds of the formulae I, Ia and Ib can be used for synthesising oligonucleotides which show valuable biological activity due to their interaction with nucleic acids and which can be used as pharmaceutical active ingredients or as diagnostics. The oligonucleotides can comprise identical or different monomer units of compounds of the formula I, Ia or Ib or monomer units of other nucleosides, the oligonucleotides comprising 2 to 200 monomer units. The oligonucleotides preferably comprise 2 to 100, particularly preferably 2 to 50, especially preferably 2 to 20, monomer units.

The oligonucleotides can be prepared in a manner known per se in DNA synthesizers which may be automated and which are commercially available together with protocols, using a wide range of methods. For example, in the case of the bridging group —P(O)O⊖— the phospho triester method, the phosphoramidite method or the H-phosphonate method can be used, all of which are familiar to a person skilled in the art. In the phosphite triester method, for example, a procedure can be followed in which the nucleosides of the formula I, Ia or Ib, in which R is H, are reacted with a protective group reagent, for example 4,4'-dimethoxytriphenylmethyl trifluoromethylsulfonate (abbreviated as DMT triflate). The compound obtained is then coupled with a solid support material, for example controlled-pore glass, which contains long-chain alkylamino groups, with the aid of a linker, for example succinic anhydride. In a separate process, the hydroxyl group of the protected compound is derivatised, for example to give a phosphoramidite, using [R'O(i-propyl$_2$N)]PCl, where R' is, for example, allyl or $\beta$-cyanoethyl. After the protective group of the material coupled with the support has been eliminated, coupling with the protected nucleoside takes place while —N(i—C$_3$H$_7$) is eliminated, any free hydroxyl groups which may exist are capped, and the phosphite formed is then oxidised to give the phosphate. After deprotection of the dimer, the reaction cycle is repeated with the protected nucleoside until an oligomer having the desired number of monomer units has been synthesised, and the product is uncoupled from the support material.

The compounds of the formulae I, Ia and Ib in which R is H have antiviral and antiproliferative properties and can therefore be used as pharmaceuticals. The oligonucleotides have good stability to degradation by nucleases (for example enzymes). Furthermore, very good pairing with nucleic acids, in particular double-stranded nucleic acids, with the formation of stable triple helices is observed. The oligonucleotides are therefore particularly suitable for antisense technology for the inactivation of nucleoside sequences in nucleic acids (see EP-A-0 266 099, WO 87/07300 and WO 89/08146). They can be used for the treatment of infections and diseases, for example by blocking bioactive proteins at the nucleic acid level (for example oncogens). The oligonucleotides are also suitable as diagnostics and can be used as gene probes for detecting viral infections or hereditary diseases by selective interaction at the level of single- or double-stranded nucleic acids. In particular, application as a diagnostic is possible not only in vitro but also in vivo (for example tissue samples, blood plasma and blood serum), due to the very good stability to nucleases. Such possible applications are described, for example, in WO 91/06556.

The examples which follow illustrate the invention.

A) Preparation examples of starting compounds

Example A1: Preparation of

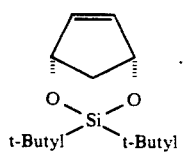

Under an argon atmosphere, a reaction bulb is charged with 0.91 g (9.1 mmol) of cis-4-cyclopentene-1,3-diol and 20 ml of anhydrous methylene chloride, and the mixture is cooled to 0° C. 3.17 ml (27.3 mmol) of lutidine are added, with stirring, and then 4.42 g (10 mmol) of di-t-butylsilyl ditriflate are added in the course of 10 minutes, with stirring. The reaction mixture is stirred for 10 minutes at 0° C., the ice-bath is then removed, and stirring is continued for 30 minutes. After this, the solvent is removed in vacuo, and the oily residue is treated with 20 ml of hexane, with vigorous stirring. The crystalline lutidinium triflate which has formed is filtered off, and the solvent is evaporated from the filtrate. The residue is chromatographed on silica gel using hexane/diethyl ether (20:1) and, after the solvent has been evaporated and the residue dried (room temperature, 30 minutes, 1.3 Pa), 1.4 g (65%) of a colourless oil are obtained. $^1$H NMR (250 MHz, CDCl$_3$): 0.96 and 1.04 (2s, 2 * CH$_3$CSi); 1.81 [dt, J=12.0 and 3.0, H—C(2)]; 2.49 [d, J=12.0, HC(2)].

If the process is repeated and five times the amount of material is used, a yield of 80% of theory is obtained.

Example A2: Preparation of

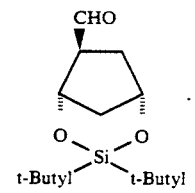

A 50 ml gold-coated autoclave is charged with 1 g (4.16 mmol) of the compound of Example A1, 15.4 mg (0.4 mol %) of RhCl[P(C$_6$H$_5$)$_3$]$_3$ and 30 ml of tetrahydrofuran, and then heated for 5 hours at 80° C. under an H$_2$/CO atmosphere at 8 MPa. After cooling, the solvent is evaporated in vacuo, and the residue is chromatographed on silica gel (hexane/ethyl acetate 9:1). The solvent is then removed in vacuo, and the residue is dried for 1 hour at room temperature and 8 Pa. 1.07 g (95%) of the title compound are obtained as a colourless oil. $^1$H NMR (250 MHz, CDCl$_3$): 1.05 and 1.06 (2s, 2 CH$_3$CSi); 1.24 [ddd, J=14.0, 3.0 and 3.0, H—C(2)]; 2.44 [d, J=14.0, H(2)]; 9.79 (s, HCO).

Example A3: Preparation of

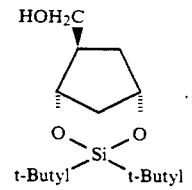

491 mg (1.82 mmol) of the compound of Example A2 are dissolved in 10 ml of tetrahydrofuran/H$_2$O(9:1) and cooled to 0° C. 34.5 mg (0.91 mmol) of NaBH$_4$ are then added in one portion with stirring, and stirring is continued for 10 minutes. The solvent is then evaporated, the residue is extracted twice using 30 ml portions of ethyl acetate, and the organic phase is washed with 20 ml portions of 2.5 percent aqueous NaHCO$_3$ and concentrated aqueous sodium chloride solution. The organic phase is then dried over Na$_2$SO$_4$ and filtered, and the filtrate is evaporated to dryness. After the residue has been dried at room temperature under a high vacuum for one hour, 485 mg (98%) of the title compound are obtained as a colourless oil which still contains a small amount of ethyl acetate. $^1$H NMR (300 MHz, CDCl$_3$): 1.04 and 1.05 (2s, 2 CH$_3$CSi); 1.38 (ddd, J=14.5, 5.0 and 5.0) and 1.47 (ddd, J=3.5, 3.5 and 13.5) and 2.30 (ddd, J=3.0, 8.5 and 14.5) and 2.42 (d, J=13.5), [H$_2$—C(2) and H$_2$C(5)]; 1.59 [s, HOCH; 3.36 [dd, J=8.5 and 10.5, HOH$_2$C(6)].

Example A4: Preparation of

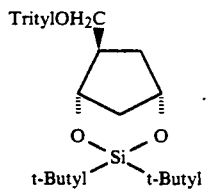

397 mg (1.46 mmol) of the compound of Example A3, 17.8 mg (0.15 mmol) of 2-dimethylaminopyridine and 405 μl (2.91 mmol) of triethylamine are dissolved in 5 ml of CH₂Cl₂ under an argon atmosphere. 528 mg (1.89 mmol) of trityl chloride are then added in one portion at room temperature while the solution is stirred, and stirring is continued for 18 hours. After this, the solvent is evaporated in vacuo, and the residue is extracted with two 50 ml portions of hexane/ethyl acetate. Hereupon the solution is washed with 30 ml portions of aqueous 6 percent NaHCOC₃ and concentrated sodium chloride solution, dried over Na₂SO₄ and filtered, the solvent is evaporated in vacuo, and the residue is dried overnight at room temperature under a high vacuum. 657 mg (88%) of the title compound are obtained. ¹H NMR (250 MHz, CDCl₃): 1.04 and 1.05 (2s, 2 (C$\underline{H}_3$CSi); 1.32–1.50 (m) and 2.22 (ddd, J=14.5, 3.0 and 9.0) and 2.35 (d, J=13,5), ]$\underline{H}_2$—C(2) and $\underline{H}_2$C(5)]; 2.66 ]m, HC(4)], 4.43–4.58 [m, $\underline{H}$—C(1.3)]; 7.17–7.47 [m, 15H—C(aromatic)].

Example A5: Preparation of

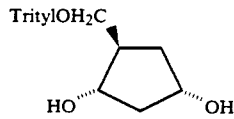

as the racemate.

A solution of 752 mg (2.39 mmol) of tetra-n-butylammonium fluoride trihydrate in 10 ml of tetrahydrofuran is added to 558 mg (1.08 mmol) of the compound of Example A4, and the mixture is stirred for 5 hours at room temperature. After this, the solvent is evaporated in vacuo, the residue is dissolved in ethyl acetate/hexane (2:1), and the solution is chromatographed over silica gel. The solvent is removed from the collected fractions by evaporation in vacuo, and the residue is then dried for 18 hours at room temperature under a high vacuum. 409 mg (quantitative yield) of the title compound are obtained as a colourless resinous substance which crystallises upon standing. Recrystallisation from ethyl acetate/hexane (1:2) gives a crystalline substance of a melting point of 116°–117° C. ¹H NMR (250 MHz, CDCl₃): 1.48 (ddd, J=5.5, 8.8 and 14.0) and 1.78 (m, 2 main signals) and 1.88–2.08 (m) [$\underline{H}_2$—C(2) and $\underline{H}_2$—(5)]; 2.51 [$\underline{H}$—C(4)]; 2.03 (d, J=5.0) and 2.58 [d, $\overline{J}$=5.0, HO—C(1.3)]; 2.93 [dd, J=8.5 and 8.5, $\underline{H}$—C(6)]; 3.21 [dd, J=5.5 and 9.0, $\underline{H}$—C(6)]; 4.09 and 4.32 [2m, $\underline{H}$—C(1.3)]; 7.18–7.46 [m, $\overline{H}$—C(aromatic)].

Example A6: Preparation of

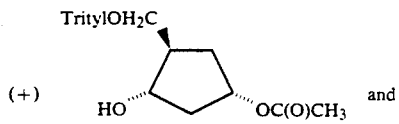

6.22 g (16.6 mmol) of the compound of Example A5 are dissolved in 63 ml of vinyl acetate and treated with 1.24 g of Pseudomonas fluorescens lipase (PFL). The heterogeneous reaction mixture is hereupon stirred for 50 hours at room temperature. The mixture is then evaporated in vacuo, the residue is taken up in hexane/ethyl acetate (2:1), and this is then chromatographed over silica gel. 250 mg of the diacetate compound, 3.38 g of pure compound (a) and 3.45 g of pure compound (b) as well as 970 mg of unseparated monoacetates are obtained, the latter being rechromatographed. The combined pure compounds (a) and (b) are dissolved three times in CH₃CN and evaporated to dryness in vacuo. 3.00 g (43.4%) of compound (a) and 3.15 g (45.5%) of compound (b) are obtained as slightly yellow oils which are still contaminated with a little CH₃CN. ¹H NMR (250 MHz, CDCl₃) of the compound (a), (1S,3S,4R)-Trans-4-trityloxy-cis-3-hydroxy-1-acetoxy-cyclopentane: 1.54 [m, $\underline{H}$-C(5)]; 1.74 [m, $\underline{H}_2$C(2)]; 1.89 [m, $\underline{H}$-C(5)]; 2.05 (s,$\underline{H}_3$CCOO); 2.40 [m, $\overline{H}$-C(2) and $\underline{H}$-C($\overline{4}$)]; 2.52 [d, J=4.0, $\overline{HO}$—C(3)]; 2.98 [t, $\overline{J}$=8.5, $\underline{H}$-C($\overline{6}$)]; 3.34 [dd, J=9.0 and $\overline{5}$.0, $\underline{H}$-C(6)]; 3.95 [dq, J=3.0 and 7.0, $\underline{H}$-C(3)]; 5.07 [m, $\underline{H}$($\overline{1}$)]; 7.21–7.45 [m, $\underline{H}$-C(aromatic)]. The compound (a) is obtained with an optical purity ee equals 98.2% (HPLC analysis, Chiracel® OD, hexane/i-propanol 9:1, flow rate 1 ml/minute). ¹H NMR (250 MHz, CDCl₃) of the compound (a), (1R,3R,4S)-trans-4-trityloxy-cis-1-hydroxy-3-acetoxy-cyclopentane: 1.61–178 [m, $\underline{H}$-C(2.5) and $\underline{HO}$-C(1)]; 1.95 [m, $\underline{H}$-C(5)]; 2.03 [s, $\underline{H}_3$—CCOO]; 2.30 [ddd, J=14.5 and $\overline{7}$.5 and 5.5, $\underline{H}$-C($\overline{2}$)]; 2.60 [m, $\underline{H}$-C(4)]; 3.12 [ABM system, $\underline{H}_2$-C($\overline{6}$)]; 4.34 [m, $\underline{H}$—$\overline{C}$(1)]; 5.05 [m, $\underline{H}$-C(3)]; 7.18–$\overline{7}$.45 [m, $\underline{H}$-C(aromatic)]. The compound (b) is obtained in optical purity of ee equals 98.6%.

Example A7: Preparation of

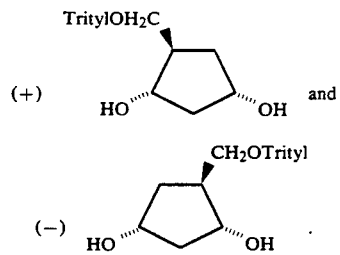

100 g (240 mmol) of the monoacetates of Example A6 are dissolved in 600 ml of methanol under argon and 188.5 g (4.8 mol) of ethylenediamine are added, during which process the temperature rises to 50° C. The reaction mixture is stirred for 15 hours at this temperature. The solvent is then evaporated under a high vacuum, the residue is taken up three times in acetonitrile and reevaporated. The resulting oil is dissolved in 500 ml of ethyl acetate, 300 ml of water are added, and aqueous citric acid solution (10%) is added with stirring. After an addition of a further 500 ml of ethyl acetate, the organic phase is separated off and the aqueous phase is extracted twice using 150 ml portions of ethyl acetate. The combined organic phases are dried over NaHCO₃ and then evaporated. The residue is taken up twice in acetonitrile and evaporated and then recrystallised from cyclohexane (1 week, 8°-10° C.). After drying, in each case 85.2 g (95%) of the title compounds are obtained as colourless crystals. The ¹H NMR spectra are identical with the racemate of Example B 1.

Compound (a): Melting point 105°-106° C.; $[\alpha]^{25}$=24.1 (589, c=1.0, CH₃OH), +73.7 (365 nm).

Compound (b): Melting point 105°-106° C.; $[\alpha]^{25}$=−25.8 (589, c=1.0, CH₃OH), 75.2 (365 nm).

B) Preparation of nucleosides

Example B 1: Preparation of

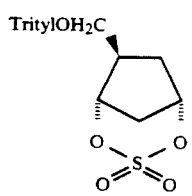

as the racemate.

a) 1.049 g (2.80 mmol) of the compound of Example A5 are dissolved in 20 ml of CH₂Cl₂ and 1.56 ml (11.4 mmol) of triethylamine under an argon atmosphere. The solution is cooled to 0° C. with stirring, and 302 μl (4.2 mmol) of SOCl₂ are added dropwise in the course of 5 minutes. The colour of the reaction mixture changes from colourless via yellow to brown, and a brown solid precipitates after 10 minutes. The reaction mixture is hereupon extracted twice using 20 ml of ice-cold water and then 30 ml of ice-cold sodium chloride solution (18 percent by volume). The organic phase is then dried over MgSO₄ and filtered, and the product is evaporated to dryness in vacuo at 15° C. The residue is dissolved twice in in each case 6 ml of CH₃CN and reevaporated to dryness, and dried for 10 minutes in a high vacuum. 1.335 g of the cyclic sulfite (113%, contains CH₃CN and triethylamine as impurities) are obtained, and this is used as such in process b) below.

b) 8.50 g of the compound prepared by the procedure of a) are dissolved in 160 ml of CH₃CN/CCl₄ (1:1) and the solution is cooled to 0° C. 120 ml of water, 47 mg (200 μmol) of RuCl₃xH₂O and 5.71 g (26.7 mmol) of NaIO₄ are then added in succession. The mixture is stirred vigorously for one hour, 300 ml of diethyl ether are then added, and the aqueous phase is separated off. The organic phase is washed three times using 100 ml of ice-cold and concentrated aqueous sodium chloride solution, dried over MgSO₄ and filtered, and the product is evaporated in vacuo at 15° C. and then dried under a high vacuum. 5.80 g (99.5%, based on the two process steps) of the title compound are obtained as a colourless and amorphous solid. ¹H NMR (250 MHz, CDCl₃): 1.61 (dt, J=13.5 and 4.0) and 1.77 (dr, J=12.5 and 2.5) and 2.69 (d, J=12.5) and 2.80-2.92 (m, partially overlapping signals) [H₂-C(2) and H₂-C(5)]; 3.39 [m, H-C(4)]; 2.84 (dd, J=8.5 and 7.5,) and 3.29 [dd, J=8.5 and 4.5, H₂-C(6)]; 5.09 (broad s) and 5.22 [broad s, H-C(1.3)]; 7.21-7.45 [m, H-C(aromatic)].

Using enantiomeric cyclopentanediols, the enantiomeric cyclic sulfates, for example the (+) enantiomer with $[\alpha]^{25}$=+9.2 at 589 nm (c=1.05, CHCl₃) are obtained in the same manner.

Example B2: Preparation of

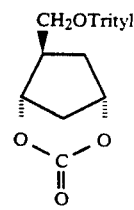

as the racemate. 200 mg (534 mmol) of the compound of Example A5 are suspended in toluene, a small amount of molecular sieve (3 Å) is added, and the mixture is stirred for approximately 5 minutes under argon. 5 minutes after the addition of 95.3 mg (588 mmol) of carbonyldiimidazole, the reaction mixture turns clear. After stirring for 36 hours at 90° C. and 45 days at room temperature, the mixture is evaporated on a rotary evaporator and the product is purified on silica gel (ethyl acetate/hexane 1:2). The pure product fractions are combined and concentrated, and this is then taken up in CH₃CN and reconcentrated. 53 mg (25%) of pure product are obtained. ¹H NMR (250 MHz, CDCl₃): i.a. 4.84 (m) and 4.78 (m)(H-C(1.3)); 3.22 (quartet-like m, H-C(4)); 2.84 (m, CH₂OTr).

Example B3: Preparation of (±)-cis-4-hydroxymethyl-1-(9-adenyl)-trans-3-hydroxycyclopentane:

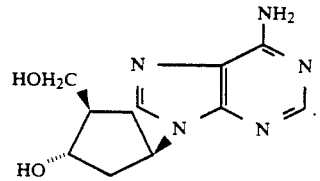

a) 297 mg (2.20 mmol) of adenine are suspended in 10 ml of CH₃CN under an argon atmosphere, and 337 mg (2.21 mmol) of 1,8-diaza-bicyclo-[5,4,0]-undec-7-ene (DBU) are then added. The mixture is stirred for 15 minutes at room temperature and subsequently treated with 0.50 g (1.15 mmol) of the racemate of Example B2. The reaction mixture is then stirred for a further 15 hours at room temperature. After the solvent has been evaporated in vacuo, the residue is taken up in CH₂Cl₂/methanol/triethylamine (30:3:1) and chromatographed on silica gel. The combined fractions are evaporated to dryness, and the residue is dissolved twice in in each case 20 ml of CH₃CN and reevaporated to dryness. The residue is then dissolved in 30 ml of water and treated with triethylamine. The precipitate is filtered and dried. 590 mg (76%) of the tetraethylammonium salt of (±)-cis-4-trityloxymethyl-1-(9-adenyl)-trans-3-sulfatocyclopentane are obtained as a colourless powder. ¹H NMR (250 MHz, CD₃OD): 1.31 [t, J=7.0, (CH₃CH₂)₃NH⁺]; 3.20 [q, J=7.0, (CH₃CH₂)₃NH⁺]; 1.64-2.66 [m, H₂-C(2.5) and H-C(4)]; 3.15-3.40 [m, H₂-C(6)]; 5.02-5.17 [m, H-C(1.3)]; 7.18-7.51 [m, H-C(trityl)]; 8.15 and 8.16 [2s, H-C(adenine)].

b) 200 mg of the compound prepared as described for a) are dissolved in each case 10 ml of 2N HCl and ethanol, and the solution is heated for 24 hours at 80°-85° C. The solvent is then evaporated in vacuo, and the residue is taken up twice in 20 ml portions of CH$_3$CN and evaporated. The crude product obtained is taken up in methanol/ethyl acetate (1:1) and chromatographed on silica gel. After the solvent has been evaporated, the residue is recrystallised using the same solvent. 80.1 mg (94%) of (+)-cis-4-hydroxymethyl-1-(9-adenyl)-trans-3hydroxycyclopentane hydrochloride as colourless crystals. $^{13}$C NMR (63 MHz, CD$_3$OD): 35.1 (C(2')), 41.7 (C(6')), 50.7 (C(4')) 55.9 (C(1')), 64.2 (C(5')), 73.7 (C(3')), 120.3, 150.3 and 151.7 (C(4,5,6)), 144.3 and 144.7 (HC(2.8)).

c) 400 mg (1.40 mmol) of the compound obtained as described for b) are dissolved in methanol and the solution is filtered through a column packed with 10 g of Amberlite IRA-93 (OH form). The collected fractions are evaporated in vacuo and the product is taken up twice in CH$_3$CN and evaporated. The residue is dissolved in methanol, the solution is refluxed, and methyl acetate is added until the mixture turns slightly cloudy. The mixture is then allowed to crystallise overnight at 4° C., and the crystals are filtered off and dried under a high vacuum. 320 mg (92%) of the title compound are obtained as colourless crystals of a melting point of 183° to 185° C. $^1$H NMR (250 MHz, CD$_3$OD): 1.94 (dt, J=12.5, 10.0) and 2.14-2.66 (m)(H$_2$—C(2',6') and H—C(4')); 3.72 (ABM system, H$_2$-C(5')); 4.32 (m, H—C(3')); 5.24 (quint.-like m, H—C(1')); 8.41 (s) and 8.48 (s)(H—C(2,8)).

Example B4: Preparation of (1R,3S,4R)-cis-4-hydroxymethyl-trans-3-hydroxy-1-(9'-adenyl)-cyclopentane.

As described in Example B 1, compound a) of Example A7 is converted into the cyclic sulfate, and 11.50 g (26.3 mmol) are reacted, as described in Example B3, with 3.76 g (27.8 mmol) of adenine. 14.25 g (80.4%) of the crystalline title compound are obtained. $^1$H NMR (250 MHz, CD$_3$OD): 1.94 (dt, J=12.5, 10.0) and 2.14-2.66 (m)(H$_2$-C(2',6') and H—C(4')); 3.72 (ABM system, H$_2$-C(5')); 4.32 (m, H—C(3')); 5.24 (quintet-like m, H—C(1')); 8.41 (s) and 8.48 (s)(H—C(2.8)).

Example B5: Preparation of (1S,3R,4S)-cis-4-hydroxymethy-trans-3-hydroxy-1-(9'-adenyl)cyclopentane.

The process is carried out as described under Example B4, except that compound (b) of Example A7 is used. 76.9% of the title compound are obtained as colourless crystals, melting point 18°-186° C., [α]$^{25}$= −10.2 (589, c=0.5, H$_2$O).

Example B6: Preparation of (1S,3R,4S)-cis-4-hydroxymethyl-trans-3-hydroxyl-(2'-chloro-6'-aminopurin-9'-yl)-cyclopentane.

Compound b of Example A7 is treated as described in Example B4, using 2-chloro-6-aminopurine, 2.0 mol equivalents of each of 6-amino-2-chloropurine and DBU being employed and the reaction time being 15 hours at 50° C. The hydrolysis is carried out for 20 hours at 80° C. in a 1:1 mixture of ethanol and 2N HCl. The yield in the first process step is 30.8% and in the second process step 63%. $^1$H NMR (300 MHz, CD$_3$OD): i.a. 5.07 (quintet-like m, H—C(1)). $^{13}$C NMR (CD$_3$OD): i.a. 55.1 (C(1)); 64.4 (C(5)); 73.8 (C(3)); 141.5 (C(8')).

Example B7: Preparation of (1R,3S,4R)-cis-4-hydroxymethyl-trans-3-hydroxy-1-(9'-guanyl)cyclopentane hydrochloride.

Using 2-amino-6-chloropurine, the procedure is as described in Example B4, the reaction time in the first process step being three hours at room temperature, and the amorphous sulfate being obtained after silica gel chromatography (CH$_2$Cl$_2$/methanol/triethylamine 50:30:1) in a yield of 75.3%. The second process step is carried out for 20 hours at 70° C. After purification by chromatography (ethyl acetate/methanol/n-methylmorpholine 25:25:1), amorphous carbacyclic 2'-deoxyquanosine is obtained in this manner in a yield of 78.4%, and this is taken up in methanol/conc. HCl (5:1) and evaporated to dryness on a rotary evaporator. Crystallisation from methanol/methyl acetate gives the title compound in a yield of 68%, of melting point 247°-248° C. (decomposition). $^1$H NMR (300 MHz, DMSO-d$_6$): i.a. 4.89 (quintet-like m, H—C(1)). $^{13}$C NMR (DMSO-d$_6$): i.a. 54.1 (C(1)); 62.5 (C(5)); 71.2 (C(3)); 135.6 (C(8')).

Example B8: Preparation of (1R,3S,4R)-cis-4-hydroxymethyl-trans-3-hydroxy-1-(2',6'-diaminopufin-9-yl)cyclopentane hydrochloride.

10.0 g (14.1 mmol) of the amorphous 2-amino-6-chloropurinecyclopentane sulfate of Example B7 are dissolved in 500 ml of methanol, the solution is injected into an autoclave, and 11 bar of ammonia are injected at 36° C. This is then allowed to react for 15 hours at 130° C. The solvent and the ammonia are subsequently removed, and the residue is taken up three times in acetonitrile and evaporated to dryness. 9.91 g (101.9%) of 2,6-diaminopurinecyclopentane sulfate are obtained. The crude product is employed in the following hydrolysis step without purification. The hydrolysis is carried out for 15 hours at room temperature as described in Example B4. The reaction product is purified by silica gel chromatography (ethyl acetate/methanol 7:3). 82.6% of the title compound, which contains approximately 5-10% of impurities, are obtained. $^1$H NMR (250 MHz, DMSO-d$_6$): i.a. 5.06 (quintet-like m, H—C(1)). $^{13}$C NMR (DMSO-d$_6$): i.a. 52.5 (C(1)); 62.6 (C(5)); 71.4 (C(3)); 139.0 (C(8')).

Example B9: Preparation of (1R,3S,4R)-cis-4-hydroxymethyl-trans-3-hydroxy-1(1'-cytidyl)cyclopentane.

The procedure is as described in Example B4 and a reaction time of 1 hour and 80° C., except that isobutyrocytosine is used. After silica gel chromatography (CH$_2$Cl$_2$/MeOH/Et$_3$N 90:3:1), the amorphous triethylammonium salt of trityl-protected isobutyrocytidyl sulfate is obtained in a yield of 61.3%. $^1$H NMR (250 MHz, CD$_3$OD): i.a. 5.04 (quintet-like m, H—C(1)). The hydrolysis is carried out for 20 hours at room temperature. After chromatographic purification (ethyl acetate/methanol/aqueous NH$_3$ 7:3:1), 86.5% of the title compound are obtained. Melting point 204°-205° C. $^1$H NMR (300 MHz, CD$_3$OD): i.a. 5.08 (quintet-like m, H—C(1)). $^{13}$C NMR (CD$_3$OD): i.a. 57.5 (C(1)); 64.2 (C(5)); 73.6 (C(3)); 146.3 (C(6')).

Example B 10: Preparation of (1R,3S,4R)-cis-4-hydroxymethyl-trans-3-hydroxy-1-(1'-thymidyl)cyclopentane.

The procedure is as described in Example B4, except that methylthymine is used. After silica gel chromatography (CH$_2$Cl$_2$/methanol/triethylamine 50:3:1), amorphous trityl-protected thymidylcyclopentane sulfate is obtained in a yield of 70.4%. $^1$H NMR (250 MHz, DMSO-d$_6$): i.a. 4.49 (m, H—C(3)) and 4.89 (quintet-like m, H—C(1')). After hydrolysis (15 hours, 45° C.) and chromatographic purification (ethyl acetate/methanol 7:1), 79.2% of the title compound are obtained as colourless crystals, melting point 175°–176° C. $^1$H NMR (300 MHz, CD$_3$OD): i.a. 5.06 (quintet-like m, H—C(1')).
$^{13}$C-NMR (CD$_3$OD): i.a. 55.9 (C(1')); 64.3 (C(5')); 73.7 (C(3')); 139.9 (C(6')).

What is claimed is:

1. A process for the preparation of an enantiomer of the formula (Ia) or (Ib)

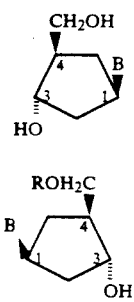

or the racemate thereof; in which R is H or a protective group, R$_1$, and B is a radical of the formula V, Va, Vb, Vc, Vd or Ve

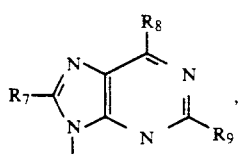

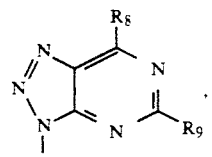

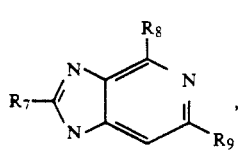

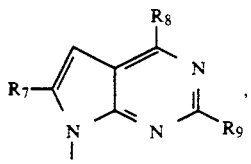

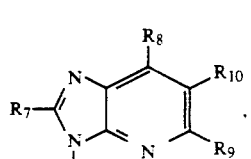

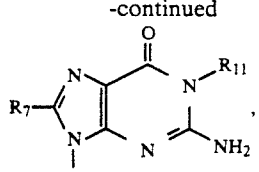

in which R$_7$ is H, Cl, Br, NH$_2$ or OH, and R$_8$, R$_9$ and R$_{10}$ independently of one another are H, OH, SH, NH$_2$, NHNH$_2$, NHOH, NHOalkyl having 1 to 12 C atoms, F, Cl, Br, alkyl or hydroxyalkyl or aminoalkyl or alkoxy or alkylthio having 1 to 12 C atoms, the hydroxyl and amino groups being unsubstituted or substituted by a protective group, phenyl, benzyl, secondary amino having 1 to 20 C atoms or tertiary amino having 2 to 30 C atoms, wherein the secondary amino and tertiary amino are radicals of the formula R$_{14}$R$_{15}$N, in which R$_{14}$ is H or independently has the meaning of R$_{15}$, and R$_{15}$ is C$_1$-C$_{20}$alkyl, -aminoalkyl, -hydroxyalkyl; carboxyalkyl or carbalkoxyalkyl, the carbalkoxy group containing 2 to 8 C atoms and the alkyl group containing 1 to 6 C atoms; C$_2$-C$_{20}$alkenyl; phenyl, mono- or di(C$_1$-C$_4$alkyl- or C$_1$-C$_4$-alkoxy-)phenyl, benzyl, mono- or di(C$_1$-C$_4$alkyl- or C$_1$-C-alkoxy)benzyl; or R$_{14}$ and R$_{15}$ together are tetra- or pentamethylene, 3-oxa-1,5-pentylene, —CH$_2$—NR$_{16}$—CH$_2$CH$_2$— or —CH$_2$CH$_2$—NR$_{16}$—CH$_2$CH$_2$—, in which R$_{16}$ is H or C$_1$-C$_4$alkyl, the amino group in aminoalkyl being unsubstituted or substituted by one or two C$_1$-C$_4$alkyl or -hydroxyalkyl groups, and the hydroxyl group in hydroxyalkyl is free or ethefified with C$_1$-C$_4$alkyl and R$_{11}$ is H or C$_1$-C$_4$alkyl; or B is a radical of the formulae VI, VIa or VIb, or the dihydro derivative thereof;

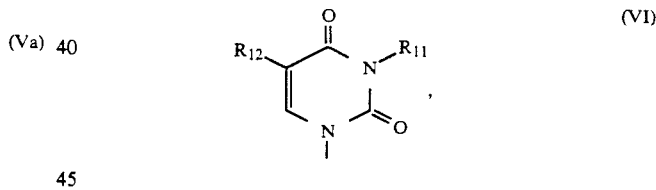

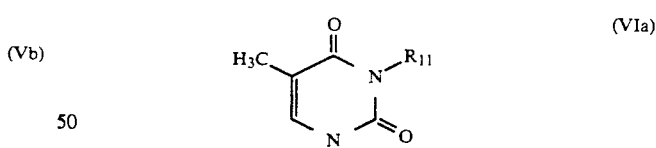

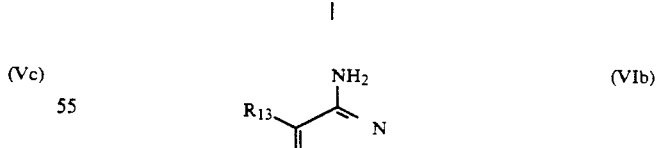

in which R$_{11}$ is H or C$_1$-C$_4$alkyl and R$_{12}$ and R$_{13}$ independently of one another are as defined for R$_8$ above and the hydrogen atoms of the NH$_2$ group in formula VIb can be substituted by C$_1$-C$_6$alkyl or benzoyl; which comprises the steps of (a) reacting an enantiomer of the formula IIa or IIb, or the racemate thereof,

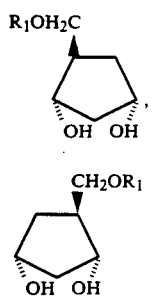 (IIa)

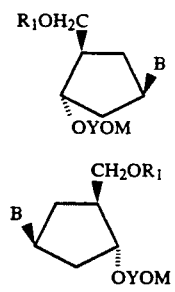 (IVa)

(IIb)

(IVb)

in which $R_1$ is a protective group, with a compound of the formulae X—CO—X, X—CS—X, X—SO—X, X—SO$_2$—X, $X_2P$—$R_6$ or $X_2P(O)$—$R_6$, in which X is a leaving group, $R_2$ is linear or branched $C_1$-$C_{18}$alkyl, $C_5$-$C_8$cycloalkyl, phenyl, benzyl, or phenyl or benzyl which are substituted by $C_1$-$C_6$alkyl or $C_1$-$C_6$alkoxy, $R_3$ and $R_4$ independently of one another are H, linear or branched $C_1$-$C_{18}$alkyl, $C_5$-$C_8$cycloalkyl, phenyl, benzyl, or phenyl or benzyl which are substituted by $C_114$ $C_6$alkyl or $C_1$-$C_6$alkoxy, or $R_3$ and $R_4$ together are tetramethylene, pentamethylene or 3-oxa-1,5-pentylene, $R_5$ is H, linear or branched $C_1$-$C_{12}$alkyl, $C_5$-$C_8$cycloalkyl, phenyl, benzyl, or phenyl or benzyl which are substituted by $C_1$-$C_6$alkyl or $C_1$-$C_6$alkoxy, and $R_6$ is linear or branched $C_1$-$C_2$alkyl or $C_1$-$C_{12}$alkoxy, $C_5$-$C_8$cycloalkyl or $C_5$-$C_8$cycloalkoxy, phenyl, or phenyloxy, benzyl or benzyloxy, or $R_6$ is phenyl or phenyloxy or benzyl or benzyloxy which are substituted by $C_1$-$C_6$alkyl or $C_1$-$C_6$alkoxy, to give an enantiomer of the formula IIIa or IIIb, or the racemate thereof,

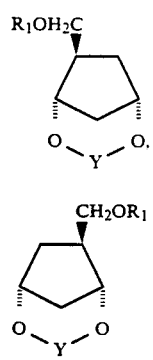 (IIIa)

(IIIb)

in which Y is selected from the group consisting of —C(O)—, —C(S)—, —SO—, —SO$_2$—, $R_6P=$ and $R_6(O)P=$ in which $R_1$ to $R_6$ are as defined above, (b) reacting the product of step (a) with a nucleic base corresponding to a radical of formula V, Va, Vb, Vc, Vd or Ve, or the alkali metal salt thereof, or a nucleic base corresponding to a radical of formula VI, VIa or VIb, or the dihydro derivative or alkali metal salt thereof, in the presence or absence of a non-nucleophilic base, to give an enantiomer of the formula IVa or IVb, or the racemate thereof, in which M is H, an alkali metal or a non-nucleophilic base and Y is as defined above, and (c) converting the product of step (b) into the compound of the formula Ia or Ib, or the racemate thereof, by eliminating the group YOM, and, when R is H, the protective group, $R_1$.

2. A process according to claim 1, in which $R_1$ is linear or branched $C_1$-$C_8$alkyl, $C_7$-$C_{12}$aralkyl, triphenylsilyl, alkyldiphenylsilyl, dialkylphenylsilyl and trialkylsilyl, each of which has 1 to 20 C atoms in the alkyl groups, $C_2$-$C_{12}$acyl, $R_{17}SO_2$, in which $R_{17}$ is $C_1$-$C_{12}$alkyl, $C_5$- or $C_6$cycloalkyl, phenyl, benzyl, $C_1$-$C_{12}$alkylphenyl, $C_1$-$C_{12}$alkylbenzyl, or halophenyl or halobenzyl, or $R_1$ is $C_1$-$C_{12}$alkoxycarbonyl, phenyloxycarbonyl, benzyloxycarbonyl, methyl- or methoxy- or chlorophenyloxycarbonyl or -benzyloxycarbonyl.

3. A process according to claim 2, in which $R_1$ is linear or branched $C_1$-$C_4$alkyl, $C_7$-$C_{12}$aralkyl, trialkylsilyl having 1 to 12 C atoms in the alkyl groups, $C_2$-$C_8$acyl, $R_{17}$—$SO_2$—, in which $R_{17}$ is $C_1$-$C_6$alkyl, phenyl, benzyl, $C_1$-$C_4$alkylphenyl, $C_1$-$C_4$alkylbenzyl or halophenyl or halobenzyl, or $R_1$ is $C_1$-$C_8$alkoxycarbonyl, phenoxycarbonyl or benzyloxycarbonyl.

4. A process according to claim 1, in which $R_1$ is methyl, ethyl, n- and i-propyl, n-, i- and t-butyl; benzyl, methylbenzyl, dimethylbenzyl, methoxybenzyl, dimethoxybenzyl, bromobenzyl; diphenylmethyl, di(methylphenyl)methyl, di(dimethylphenyl)methyl, di(methoxyphenyl)methyl, di(dimethoxyphenyl)methyl, trityl, tri(methylphenyl)methyl, tri(dimethylphenyl)methyl, tri(methoxyphenyl)methyl, tri(dimethoxyphenyl)methyl, monomethoxytrityl, dimethoxytrityl; pixyl; trimethylsilyl, triethylsilyl, tri-n-propylsilyl, i-propyl-dimethylsilyl, t-butyl-dimethylsilyl, t-butyl-diphenylsilyl, n-octyl-dimethylsilyl, (1,1,2,2-tetramethylethyl)-dimethylsilyl; acetyl, propanoyl, butanoyl, pentanoyl, hexanoyl, benzoyl, methylbenzoyl, methoxybenzoyl, chlorobenzoyl and bromobenzoyl; methyl-, ethyl-, propyl-, butyl-, phenyl-, benzyl-, p-bromo-, p-methoxy- and p-methylphenylsulfonyl; methoxy-, ethoxy-, n- or i-propoxy- or n-, i- or t-butoxycarbonyl, or phenyloxycarbonyl, benzyloxycarbonyl, methyl- or methoxy- or chlorophenyloxycarbonyl or -benzyloxycarbonyl.

5. A process according to claim 1, wherein the protective group $R_1$ and the group YOM are eliminated simultaneously or in succession in process step c).

6. A process according to claim 1, wherein, in formulae V to Ve, the protective group for hydroxyl and amino groups is $C_1$-$C_8$acyl.

7. A process according to claim 1, wherein primary amino contains 1 to 12 C atoms and secondary amino 2 to 12 C atoms.

8. A process according to claim 1, wherein the secondary amino and tertiary amino are radicals of the formula $R_{14}R_{15}N$, in which $R_{14}$ is H or independently has the meaning of $R_{15}$, and $R_{15}$ is $C_1-C_{20}$alkyl, -aminoalkyl, -hydroxyalkyl; carboxyalkyl or carbalkoxyalkyl, the carbalkoxy group containing 2 to 8 C atoms and the alkyl group containing 1 to 6, preferably 1 to 4, C atoms; $C_2-C_{20}$alkenyl; phenyl, mono- or di($C_1-C_4$alkyl- or -alkoxy)phenyl, benzyl, mono- or di($C_1-C_4$alkyl- or -alkoxy)benzyl; $R_{14}$ and $R_5$ together are tetra- or pentamethylene, 3-oxa-1,5-pentylene, $-CH_2-NR_{16}-CH_2CH_2-$ or $-CH_2CH_2-NR_{16}-CH_2CH_2-$, in which $R_{16}$ is H or $C_1-C_4$alkyl, the amino group in aminoalkyl being unsubstituted or substituted by one or two $C_1-C_4$alkyl or -hydroxyalkyl groups, and the hydroxyl group in hydroxyalkyl is free or etherified with $C_1-C_4$alkyl.

9. A process according to claim 8, wherein the and tertiary amino secondary amino are methyl-, ethyl-, dimethyl-, diethyl-, allyl-, mono- or di-1-(2-hydroxyethyl)-, phenyl- and benzyl-, acetyl- and benzoylamino.

10. A process according to claim 1, wherein $R_7$ in formulae V, Vb, Vc, Vd and Ve is hydrogen.

11. A process according to claim 1, wherein $R_{10}$ in formula Vd is hydrogen.

12. A process according to claim 1, wherein $R_8$ and $R_9$ in formulae V, Va, Vb, Vc, Vd and Ve independently of one another are H, F, Cl, Br, OH, SH, $NH_2$, NHOH, $NHNH_2$, methylamino, dimethylamino, benzoylamino, methoxy, ethoxy and methylthio.

13. A process according to claim 1, wherein, in formulae I, Ia and Ib, B is selected from the group consisting of adenine, N-methyladenine, N-benzoyladenine, 2-methylthioadenine, 2-aminoadenine, 6-hydroxypurine, 2-amino-6-chloropurine, 2-amino-6-methylthiopurine, guanine, N -isobutyrylguanine.

14. A process according to claim 1, wherein the group YOM is eliminated hydrolytically in process step c).

15. A process according to claim 1, wherein $R_{11}$ in formulae VI and VIa is H or methyl.

16. A process according to claim 1, wherein $R_{12}$ in formula VI is H, $C_1-C_6$alkyl or -hydroxyalkyl, F, Cl, Br, $NH_2$, benzoylamino, mono- or di-$C_1-C_6$alkylamino.

17. A process according to claim 1, wherein $R_{13}$ in formula VIb is H, $C_1-C_6$alkyl or -alkoxy or -hydroxyalkyl, F, Cl, Br, $NH_2$, benzoylamino, mono- or di- $C_1-C_6$alkylamino.

18. A process according to claim 16, wherein $R_{12}$ is H, F, Cl, Br, $NH_2$, $NHCH_3$, $N(CH_3)_2$ or $C_1-C_4$alkyl.

19. A process according to claim 17, wherein $R_{13}$ is H, $C_1-C_4$alkyl, $NH_2$, $NHCH_3$ or $(CH_3)_2N$.

20. A process according to claim 1, wherein the radicals B in formulae I, Ia and Ib are pyrimidine radicals are derived from uracil, thymine, cytosine, 5-fluorouracil, 5-chlorouracil, 5-bromouracil, dihydrouracil and 5-methylcytosine.

21. A process according to claim 1, wherein $R_2$ is $C_1-C_{12}$alkyl, $C_5-$ or $C_6$cycloalkyl, phenyl, benzyl, or phenyl or benzyl which are substituted by $C_1-C_4$alkyl or $C_1-C_4$alkoxy.

22. A process according to claim 1, wherein $R_3$ and $R_4$ are H, $C_1-C_{12}$alkyl, $C_5-$ or $C_6$cycloalkyl, phenyl or benzyl, or phenyl or benzyl which are substituted by $C_1-C_4$alkyl or $C_1-C_4$alkoxy.

23. A process according to claim 1, wherein $R_5$ is $C_1-C_6$alkyl, $C_5-$ or $C_6$cycloalkyl, phenyl or benzyl, or phenyl or benzyl which are substituted by $C_1-C_4$alkyl or $C_1-C_4$alkoxy.

24. A process according to claim 1, wherein $R_6$ is $C_1-C_6$alkyl or -alkoxy, $C_5-$ or $C_6$cycloalkyl or -cycloalkoxy, phenyl or phenyloxy, benzyl or benzyloxy, or phenyl, phenyloxy, benzyl or benzyloxy which are substituted by $C_1-C_4$alkyl or $C_1-C_4$alkoxy.

25. A process according to claim 1, wherein the leaving group X is halide, $C_1-C_6$alkoxy, phenoxy, benzyloxy or open chain or cyclic secondary amino having 2 to 12 C atoms.

26. A process according to claim 1, wherein process steps a) and b) are carried out in an inert solvent.

27. A process according to claim 1, wherein, in process step a), the reaction is carried out using a compound of the formula X—CO—X in which X is imidazolyl, or using a compound of the formula X—SO—X in which X is Cl or Br, and the resulting cyclic sulfoxide compound is subsequently oxidised to give the cyclic sulfodioxide compound.

28. A process according to claim 1 wherein the reaction temperature in process step a) is $-20°$ to $200°$ C.

29. A process according to claim 14, wherein the group YOM is eliminated using dilute aqueous mineral acids in alcoholic solution.

30. A process according to claim 1, wherein acid-binding agents are concomitantly used in process step a) if acids HX are formed in the reaction.

31. A process according to claim 1, wherein tertiary amines are used as acid-binding agents.

32. A process according to claim 1, wherein the acid-binding agent is used in excess.

33. A process according to claim 1, wherein the leaving group X is chloride, bromide, methoxy, ethoxy or imidazolyl.

34. A process according to claim 1, wherein an excess of the reactant used for introducing the group Y is employed in process step a).

35. A process according to claim 1, wherein a non-nucleophilic base is concomitantly used in process step b).

36. A process according to claim 35, wherein the non-nucleophilic base is 1,8-diazabicyclo-[5,4,0]-undec-7-ene.

37. A process according to claim 1, wherein the reaction temperature in process step b) is $-20°$ to $200°$ C.

* * * * *